(12) United States Patent
Morgan et al.

(10) Patent No.: US 10,098,712 B2
(45) Date of Patent: Oct. 16, 2018

(54) INTEGRATED DENTAL IMPLANT ABUTMENTS

(71) Applicant: Bicon, LLC, Boston, MA (US)

(72) Inventors: Vincent J. Morgan, Boston, MA (US); Robert E. Vasile, Westborough, MA (US)

(73) Assignee: Bicon, LLC, Boston, MA (US)

( * ) Notice: Subject to any disclaimer, the term of this patent is extended or adjusted under 35 U.S.C. 154(b) by 50 days.

(21) Appl. No.: 14/591,654

(22) Filed: Jan. 7, 2015

(65) Prior Publication Data

US 2016/0193016 A1 Jul. 7, 2016

(51) Int. Cl.
*A61C 8/00* (2006.01)
*A61C 9/00* (2006.01)

(52) U.S. Cl.
CPC .......... *A61C 8/0071* (2013.01); *A61C 8/0048* (2013.01); *A61C 8/0095* (2013.01); *A61C 9/004* (2013.01)

(58) Field of Classification Search
CPC .................................................. A61C 8/0048
See application file for complete search history.

(56) References Cited

U.S. PATENT DOCUMENTS

| 5,829,977 | A | * | 11/1998 | Rogers ............. A61C 8/005 433/172 |
| 6,290,500 | B1 | | 9/2001 | Morgan et al. |
| 2003/0082499 | A1 | | 5/2003 | Halldin et al. |
| 2005/0244789 | A1 | | 11/2005 | Crohin et al. |
| 2011/0229850 | A1 | | 9/2011 | Bretton et al. |
| 2012/0035889 | A1 | | 2/2012 | Lawitschka et al. |

OTHER PUBLICATIONS

International Search Report and Written Opinion in corresponding Application No. PCT/US2016/012520, dated May 12, 2016, pp. 1-12.

* cited by examiner

*Primary Examiner* — Jacqueline Woznicki
(74) *Attorney, Agent, or Firm* — Fish & Richardson P.C.

(57) ABSTRACT

A dental abutment having a coronal portion for supporting a prosthesis separated from a post for seizing, galling or cold welding in a dental implant by a cylindrical portion and hemispheric base portion of length less than the combined length of the prosthetic head and locking taper post portions. The hemispherical portion of the abutment having a sloping shoulder with a surface that forms a small angle with a perpendicular to the cylindrical surface. A dental prosthesis system including such dental abutments.

17 Claims, 10 Drawing Sheets

INTEGRATED DENTAL IMPLANT ABUTMENTS

FIELD

The present disclosure concerns dental implant abutments.

BACKGROUND

Dental implants are often the best treatment for missing teeth. When a damaged or decayed tooth is removed, both the visible part of the tooth, called the crown, and the root are lost.

A dental implant can be placed in the jawbone so that it can be fused with natural bone and become a strong and sturdy foundation for replacement teeth. Implants can be used to replace an individual tooth or for an implant-supported bridge or denture containing multiple teeth.

A dental implant abutment is a device that connects the prosthetic tooth/teeth to the dental implant. The replacement tooth is custom made to match a patient's natural teeth and is sometimes referred to as a crown or dental prosthesis.

SUMMARY OF THE INVENTION

This disclosure describes dental abutments that can not only be used for all conventional restorative techniques, but can also be readily scanned digitally, which enables precise restorations of a tooth or teeth to be fashioned more easily and conveniently than abutments whose geometry preclude the use of digital scanning or require modification or interpretation of scanned images for use. This feature supports the movement of the dental implant field toward precise customizable prosthetic restorations and digital dentistry with the increased use of CAD/CAM technologies.

The dental abutments described within can also include anti-rotational features for the prosthetic component (i.e. crown) that allows the patient's prosthesis to have a precise fit. Grooves on opposite sides of the coronal end of the abutment (i.e. longitudinal end of abutment located farthest from the bone in the implanted site) provide the anti-rotation element. Each groove is generally of a constant depth that slopes toward the shoulder to end the anti-rotational element. The sloping of the groove is symmetric to reduce material stress. The coronal end of the abutment can also have a rough surface (e.g., a grit-blasted surface) to facilitate retention. For example, grit blasting can provide asperities up to 300 microns in size. The term "asperities" is used to indicate sharp, rough, or rugged projections extending from a surface.

The described dental abutments have a post in the area of the apical end of the abutment (i.e. longitudinal end located closest to the bone in the implanted site) that is received by the open end of the dental implant. The post allows for a 360° of rotation during seating to increase the likelihood of correct orientation of the abutment, or abutment-restoration unit, either intra-orally or extra-orally. This 360° rotation also facilitates parallelism for angled abutments. The post and implant connection utilizes a friction fit connection which is a locking taper. Once fully engaged, this mechanism limits or prevents unintentional rotation between the dental abutment and implant and can provide a bacterially sealed connection. The post has a cylindrical shape for simplicity and compatibility with a large number of dental implants.

Some dental abutments include a coronal portion that slopes to a shoulder of the dental abutment after a fixed distance of at least a 15° angle to allow for the scanning to be performed without any additional modifications or interpretations to the scan. The distance from the coronal end to the shoulder and the shoulder width has a ratio of less than seven with a shoulder width of greater than 0.02 inches. The team that developed the present dental abutments has found that the width of the shoulder and the ratio between the distance from the coronal end to the shoulder and the shoulder width to be particularly significant in providing an abutment that is conducive to digital scanning The coronal portion slopes toward the shoulder of the dental abutment at about a 3° angle to allow the anti-rotational element to work properly.

In some dental abutments, the distance from the bevel at the coronal end to the top of the hemispherical shoulder is long enough to allow all the edges of the dental abutment to be digitally scanned without additional modifications or interpretations. In contrast, other dental abutments have margins that are not smooth and/or not visible on scans so users manually draw in the margin on the scan results.

The geometry of these dental abutments also allows for one conventional recording sleeve configuration to suffice for registering multiple different abutment dimensions, since different abutment sizes and angulations are independent of the prosthetic attachment aspect of the abutment. Conventional dental impression materials can be used to record and represent multiple different abutment dimensions prosthetically.

DETAILED DESCRIPTION

Figure 1A:
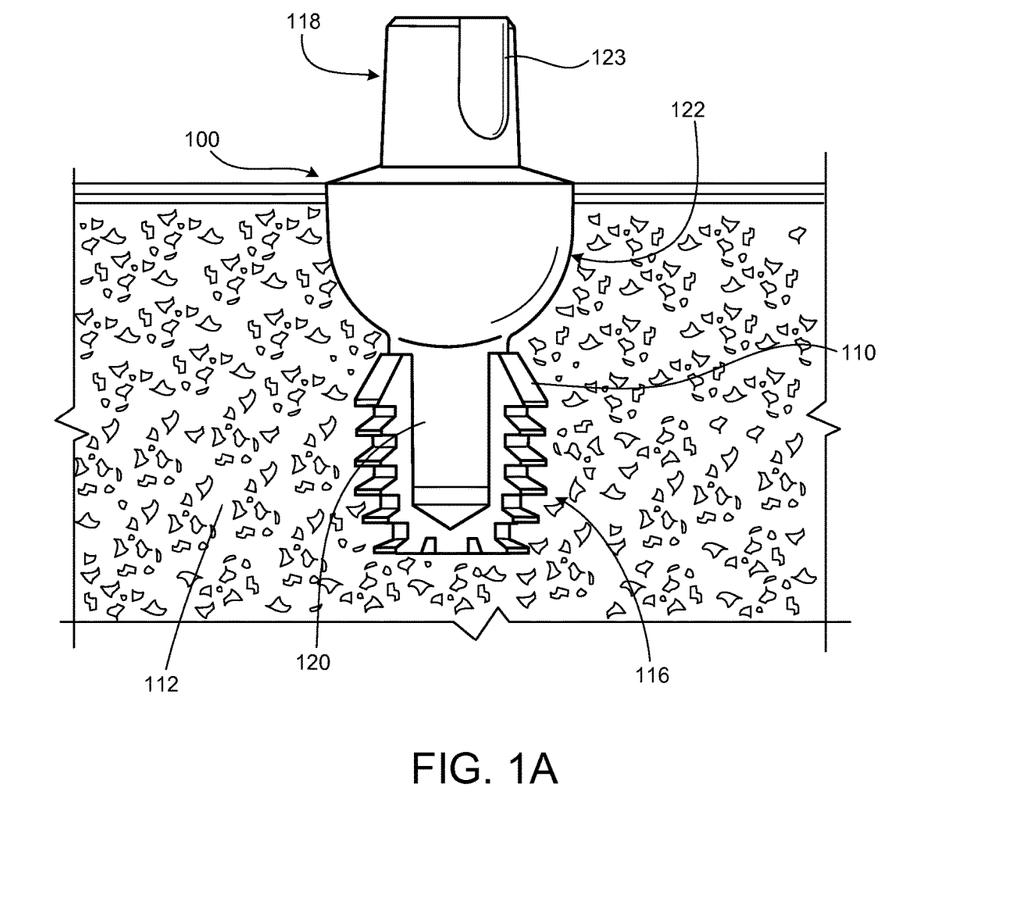
FIGS. 1A and 1B show a dental implant and dental abutment before and after the addition of a crown, respectively.
Figure 1B:
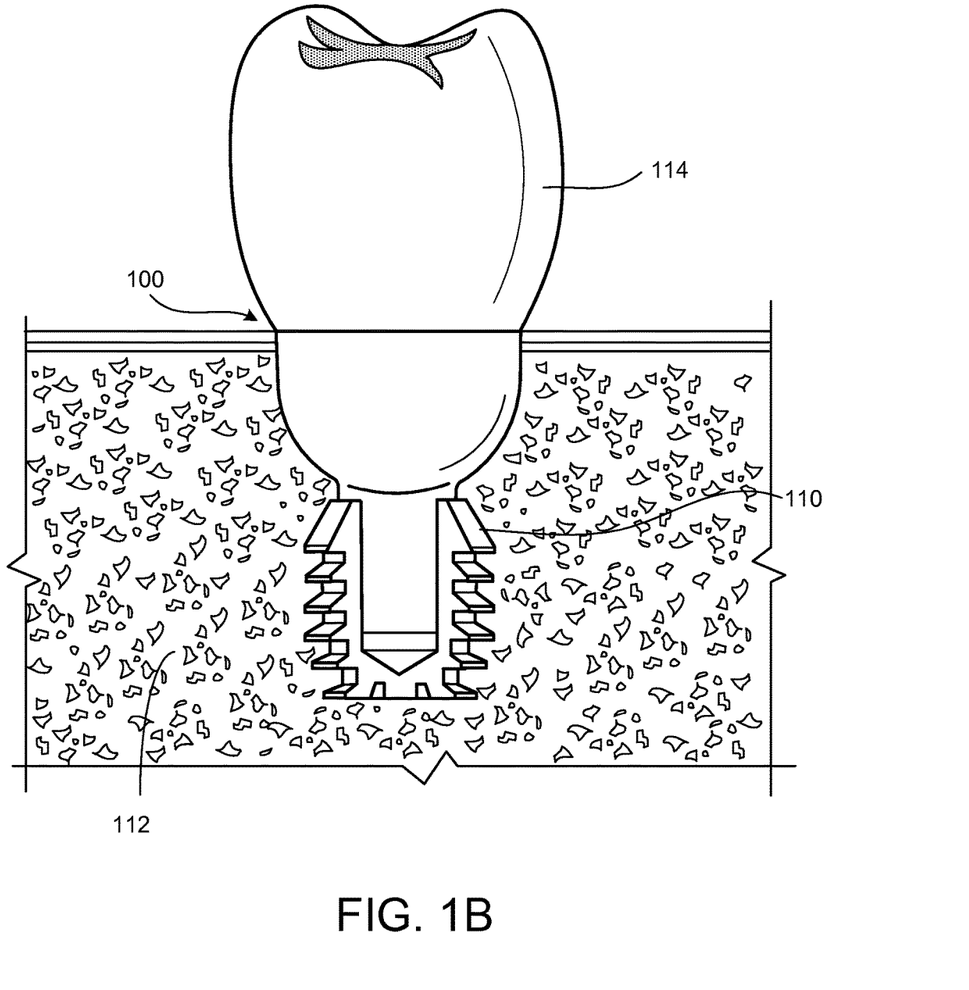

FIG. 1A shows a dental abutment 100 engaged in a dental implant 110 which has been placed in a patient's jawbone 112. FIG. 1B shows the dental abutment 100 and the dental implant 110 after a crown 114 has been placed on the dental abutment 100.

The dental abutment 100 in FIG. 1A extends from the apical end 116 (i.e. toward the jaw) to the coronal end 118 (i.e. toward the crown) in the longitudinal direction. The dental abutment 100 has a post 120, which is designed to be received by the open end of the dental implant 110. The post 120 extends from the apical end 116 of the dental abutment 100 to a retention element 122. The dental abutment 100 also has a coronal portion (or head) 123 which designed to support the crown 114. The coronal portion 123 extends from the coronal end 118 of the dental abutment 100 to the retention element 122.

The dental abutment 100 can be made out of a variety of materials, including titanium alloy or polyether ether ketone (PEEK).

Figure 2A:
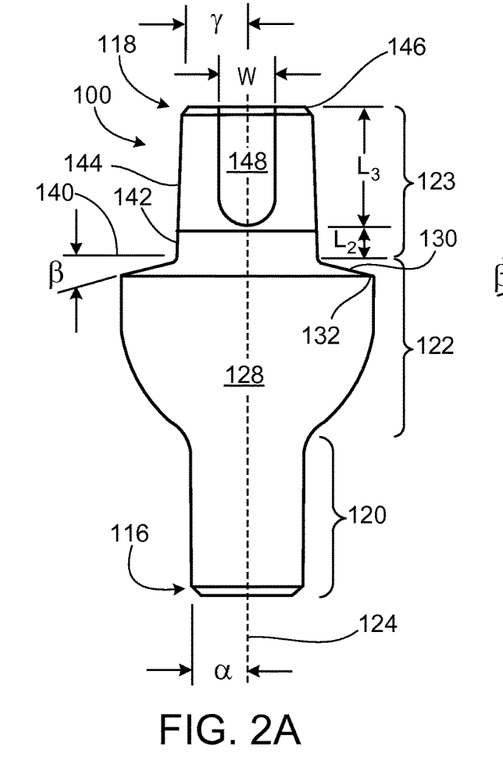
FIG. 2A is a side view of a dental abutment.
Figure 2B:
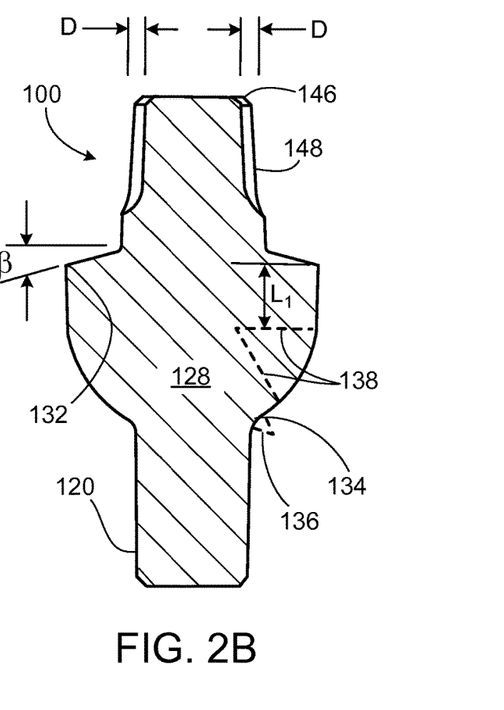
FIGS. 2B and 2C depict the cross section and coronal views of the abutment in FIG. 2A, respectively.
Figure 2C:
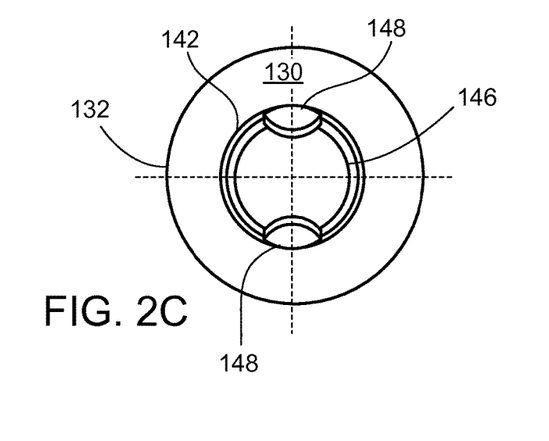

FIGS. 2A-2C shows the dental abutment 100 in isolation to more clearly illustrate features of the dental abutment 100.

The post 120 is substantially cylindrical, which allows for the 360° rotation of the dental abutment 100 while it is being seated into the dental implant 110 (see FIGS. 1A and 1B) in order to facilitate a dentist's correct orientation of the prosthesis or crown 114 (see FIG. 1B), either intra-orally or extra-orally. This cylindrical shape provides the opportunity for the prosthesis to be used to orient and initially seat the abutment in the well of the implant. The simplicity of the cylindrical shape affords for improved manufacturability and also makes the dental abutment 100 compatible with a number of different types of dental prostheses. While substantially cylindrical, the post 120 is tapered to provide a friction fit connection which is a locking taper between the post 120 and the dental implant 110 (see FIGS. 1A and 1B). This configuration can facilitate seizing, galling or cold welding between the post 120 and the dental implant 110.

Once fully engaged, this mechanism limits or prevents unintentional rotation and micro-movement between the dental abutment 100 and dental implant 110 (see FIGS. 1A and 1B). The locking taper can also provide a bacterial seal between the two components. The angle α between sides of the post 120 and a longitudinal axis 124 of the dental abutment 100 is approximately 1.3°. Depending on the dental abutment variant, the angle between sides of the post 120 and a longitudinal axis 124 of the dental abutment 100 is typically between 1.1° and 1.6°. The geometry of the dental abutment 100 is symmetrical along the longitudinal axis 124.

The retention element 122 extends from the post 120 to the coronal portion 123. The retention element 122 has a base 128 and a shoulder 130 which meets the base 128 at a margin 132. The transition between the base 128 and the post 120 is a curve 134 with a radius of curvature 136 (see FIG. 2B) of approximately 0.02 inches. In some dental abutments, the radius of curvature 136 is more or less than 0.02 inches (e.g., between 0.01 and 0.03 inches) which can reduce stress factors and resulting fractures. The surface of the base 128 has a radius of curvature 138 (see FIG. 2B) of approximately 0.08 inches. In some dental abutments, the radius of curvature 138 is more or less than 0.08 inches (e.g., between 0.08 and 0.15 inches). The shape of the base 128 provides for the consistent confrontation of what is an approximation of a hemispherical contour to tissues in the proximity to the periosteum. This confrontation in turn can stimulate osteoblastic activity and subsequent bone growth.

Between the hemisphere and the shoulder 130, the side of the abutment extends for a length $L_1$ to the margin 132. The perimeter (e.g., circumference) of the dental abutment increases at 1-2° in this portion of the dental abutment as distance from the apical end 116 of the dental abutment 100. In the dental abutment 100, the length $L_1$ is 0.16 inches (4 mm). As discussed in more detail below with reference to FIGS. 3A and 3B, some dental abutments are configured in which the length $L_1$ is more or less than 0.16 inches (4 mm) (e.g., between 0.05 (1.3 mm) and 0.32 inches (8.1 mm)). This variability provides the opportunity to use the same inferior or post and superior or head contours on the abutment, while providing the flexibility to use with implants placed at different depths within the jaw bone.

The diameter of the dental abutment at the margin 132 is 0.24 inches (6 mm). In some dental abutments, the diameter of the dental abutment at the margin 132 is more or less than 0.24 inches (6 mm) (e.g., between 0.16 inches (4 mm) and 0.31 inches (8 mm)).

An angle β is defined between the shoulder 130 and a plane 140 that is perpendicular to the longitudinal axis 124. In dental abutment 100, the angle β is approximately 15°. In some dental abutments, the angle β is more or less than 15° (e.g., between 10° and 20°). It has been found that dental abutments in which the angle β is approximately 15° allow the scanning to be performed without any additional modifications or interpretations to the scan.

The coronal portion 123 includes a neck 142, an anti-rotation portion 144, and a bevel 146 at the coronal end of the dental abutment 100. The neck 142 has a length $L_2$. The neck 142 is substantially cylindrical with sides that are substantially parallel to the longitudinal axis 124 of the dental abutment 100. Some dental abutments have necks with other shapes such as, for example, with rectangular or octagonal (rather than circular) cross-sections.

In contrast, the anti-rotation portion 144 of the coronal portion 123 is tapered with a cone angle γ such that the perimeter (e.g., circumference) of the coronal portion 123 at the coronal end of the anti-rotation portion 144 is smaller than the apical end of the anti-rotation portion 144. In dental abutment 100, the cone angle γ is approximately 3°. In some dental abutments, the angle γ is more or less than 3° (e.g., between 2.5° and 3.5°). It has been found that dental abutments in which the angle γ is more than 2.5° help enable scanning to be performed without any additional modifications or interpretations to the scan.

The surface of coronal portion 123 can be either rough or smooth based on the individual needs dictated by the procedure. A roughened surface can be achieved, for example, through the use of grit blasting. This provides a better surface for the adhesion of dental materials, such as opaque (i.e., composite dental resin that is used to cover unsightly dentition), as well as the crown 114 or prosthesis to the coronal portion 123. In particular, the roughened surface can facilitate the mechanical retention of chemical bonding agents such as opaque layers of composite resins or prosthetic cementing agents.

The structure of the coronal portion 123 provides the dental abutment 100 with a configuration that can be easily scanned. The perimeter (e.g., the circumference) of the dental abutment 100 increases monotonically from the coronal end 118 to the margin 132 defined between the base 128 and the shoulder. The edge between the bevel 146 and the anti-rotation portion 144 is smaller than the edge between anti-rotation portion 144 and the neck 142. The edge between the anti-rotation portion 144 and the neck 142 is smaller than margin 132 between the neck 142 and the base 128. As can be seen best in FIG. 2C, the shoulder 130 is visible and clearly delineated which makes the shoulder 130 easy to record during digital scanning In addition, the length $L_3$ (from the bevel 146 to the neck 142 of the coronal portion 123) is long enough that when present in concert with angle γ, allows all the edges of the dental abutment to be observed with a digital scanner without additional modifications or interpretations to the scan. Unlike abutments whose geometry preclude the use of digital scanning or require modification or interpretations of scanned images for use, the abutments presented in this application allow for easy digital scanning which enables the rapid and precise restorations of a tooth or teeth. This feature supports movement of the dental implant field toward customizable restorations or prostheses and digital dentistry with the increased use of CAD/CAM technologies.

The geometry of these dental abutments not only facilitate their recording by digital scanning technologies, but also allows for a singular conventional recording sleeve configuration to suffice for registering multiple different abutment dimensions. Further conventional dental impression materials can be used to record and represent their multiple different abutment dimensions prosthetically.

The anti-rotation portion 144 of the coronal portion 123 includes anti-rotation features in the form of two grooves 148 on opposite sides of the coronal end 118. The anti-rotational features help control the orientation of a prosthetic component or crown 114 which helps provide a precise fit of the prosthesis. The grooves also guide the prosthetic component or crown 114 into the correct orientation.

The anti-rotation grooves 148 located on opposite sides of the coronal end 118 of the dental abutment 100 are generally of a constant depth that slopes toward the shoulder to end the anti-rotational element. The sloping of the groove is symmetric to reduce material stress.

The length $L_3$ (see FIG. 2A) of the anti-rotation portion 144 and the grooves 148 are nominally 0.125 inches (3.2 mm). The width W (see FIG. 2A) of the grooves 148 is nominally 0.055 inches (1.4 mm). The depth D (see FIG. 2B) of the grooves 148 is nominally 0.02 inches (0.51 mm). As discussed above, the anti-rotation portion 144 of the coronal portion 123 is tapered with an angle γ of approximately 3°. The angled surface allows the anti-rotational element (e.g., grooves 148) to work properly. In addition, the sloping surface facilitates attaching other components as it is difficult to attach additional components to parallel surfaces, Some dental abutments have grooves 148 in which the length $L_3$ is more or less than 0.125 inches (3.2 mm) (e.g., between 0.1 (2.5 mm) and 0.3 inches (7.6 mm)), the width W is more or less than 0.055 inches (1.4 mm) (e.g., between 0.04 inches (1 mm) and 0.06 inches (1.5 mm)), and/or the depth D is more or less than 0.02 inches (0.51 mm) (e.g., between 0.010 inches (0.254 mm) to 0.030 inches (0.76 mm)). Some dental abutments include other anti-rotation features such as, for example, hexagonal or multi-sided flat surfaces and/or a variety of slots or grooves.

As discussed above, some dental abutments are configured in which the length $L_1$ (between the hemispherical portion of the base 128 and the margin 132) is more or less than 0.16 inches (4 mm) (e.g., between 0.06 inches (1.5 mm) and 0.32 inches (7 mm)).

Figure 3A:
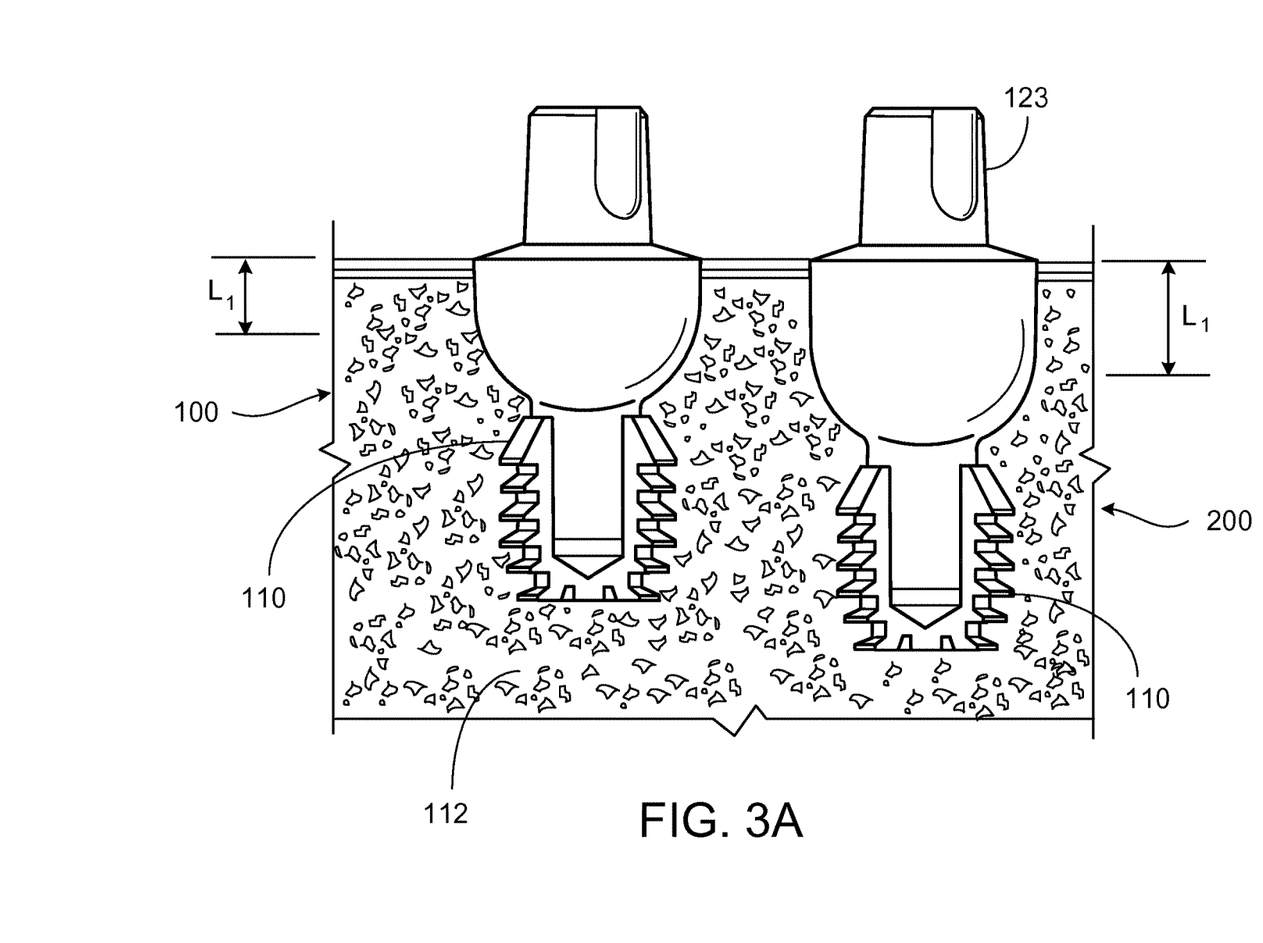
FIGS. 3A and 3B show two dental abutments of different sizes with and without a crown.
Figure 3B:
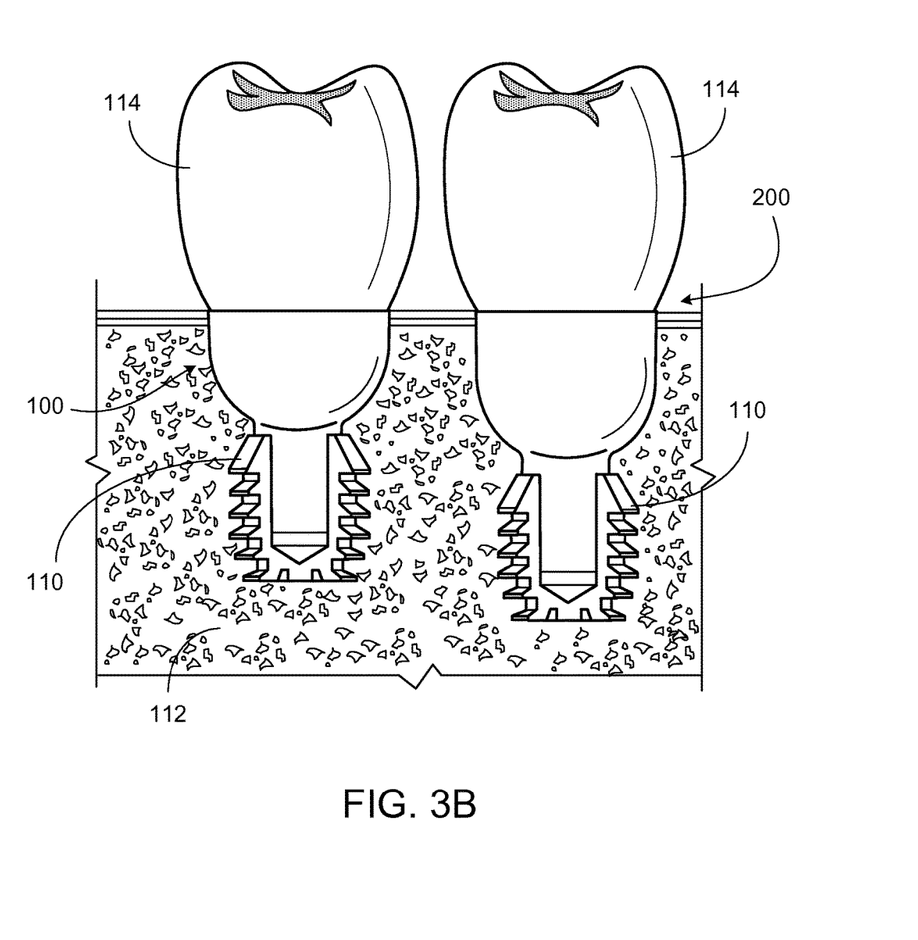

FIGS. 3A and 3B compare the dental abutment 100 with a dental abutment 200 that has a length $L_1$ that is 0.24 inches (~6 mm). The dental abutment 100 and the abutment 200 have identical configurations except for the differences in the length $L_1$. In particular, the dimensions of the post 120 are the same in both the dental abutment 100 and the abutment 200 such that a single type of dental implant can be used with either abutment. This configuration allows a dentist to set the position of the coronal portion 123 of the dental abutment 100, 200 relative to the gum above an implant regardless of the implant's axial position in the jawbone 112.

Figure 4A:
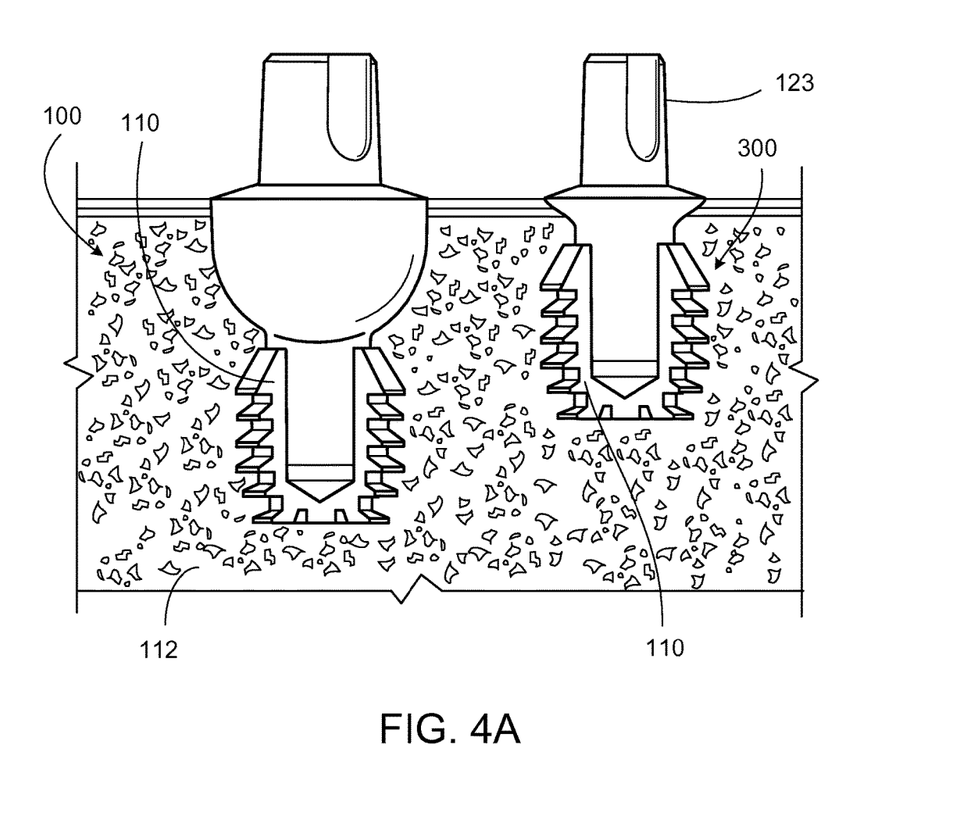
FIGS. 4A and 4B show two dental abutments of different configurations with and without a crown.
Figure 4B:
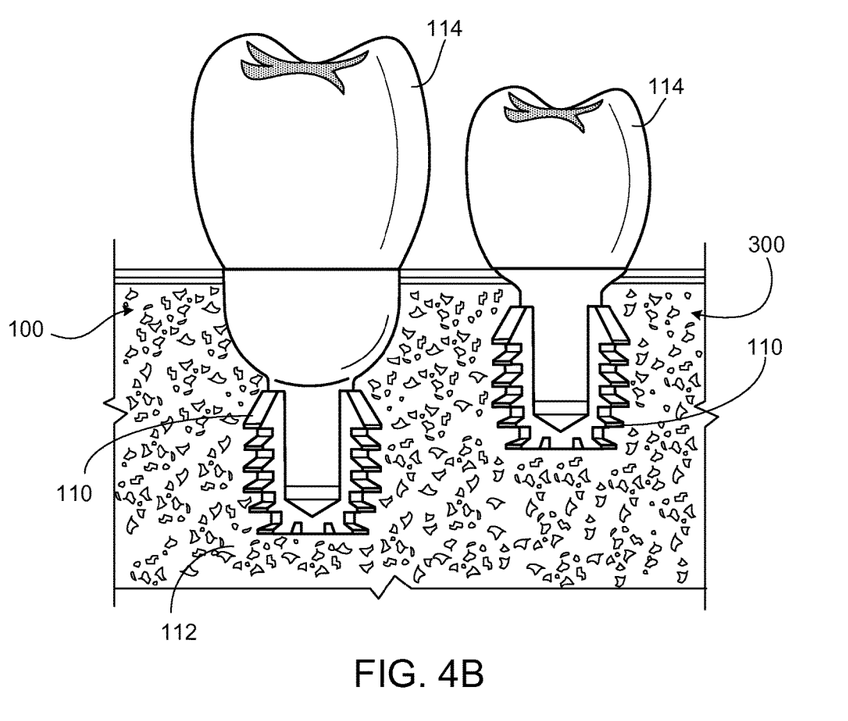

Some dental abutments have retention elements 122 that have different perimeters (e.g., diameters for the illustrated dental abutments). FIGS. 4A and 4B compare the dental abutment 100 with a dental abutment 300 in which both length L1 and the diameter of the retention element are smaller than those of the dental abutment 100. It accommodates implant wells that are more parallel for greater retention or wider for greater strength and resistance to metal fatigue and breakage.

Figure 5A:
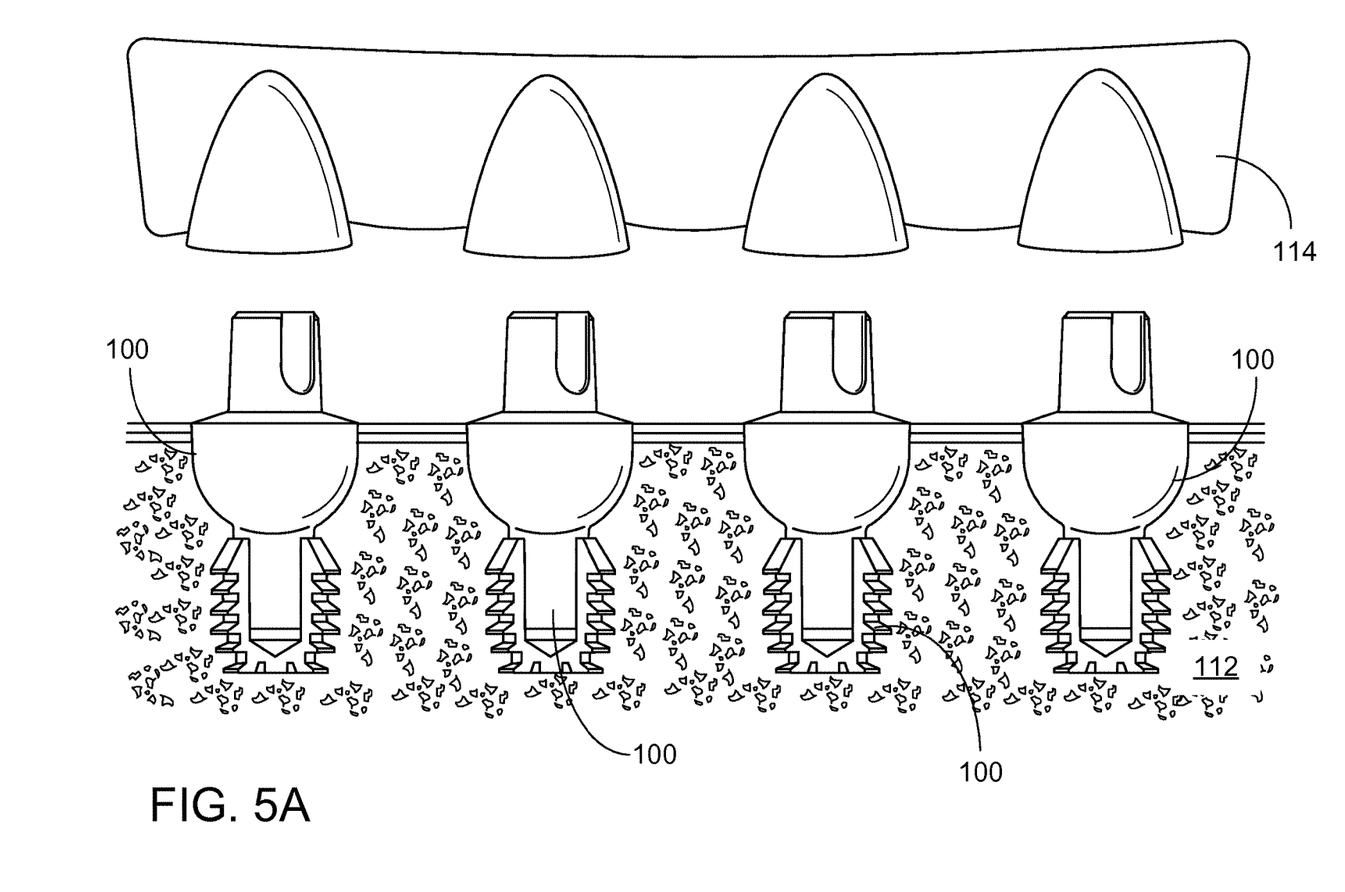
FIGS. 5A-5C show a dental prosthesis supported by multiple dental abutments.
Figure 5B:
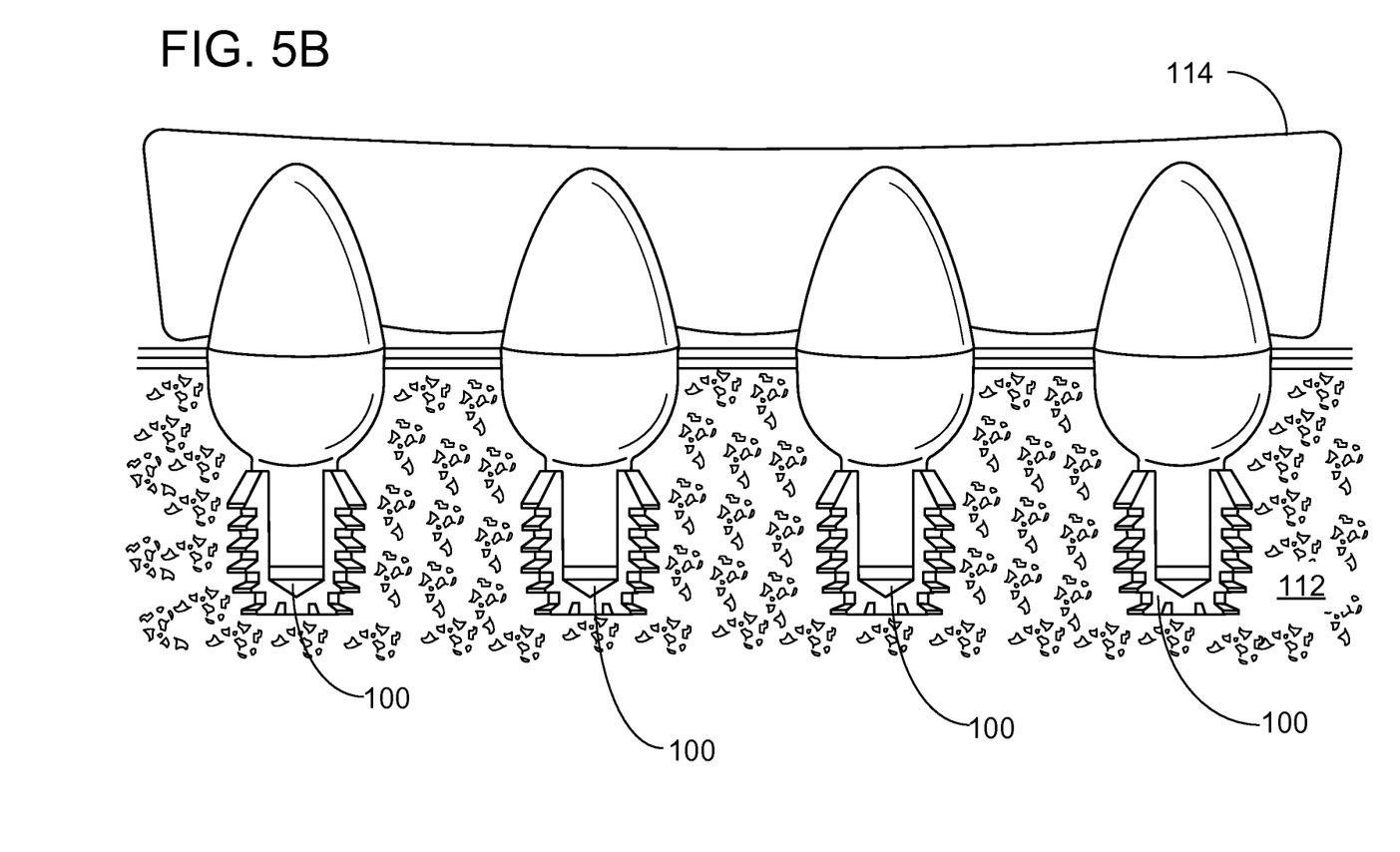
Figure 5C:
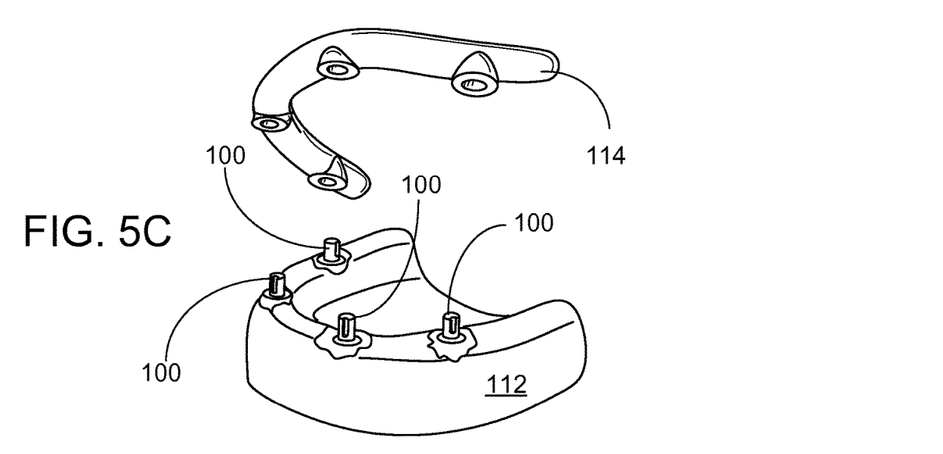
Figure 6A:
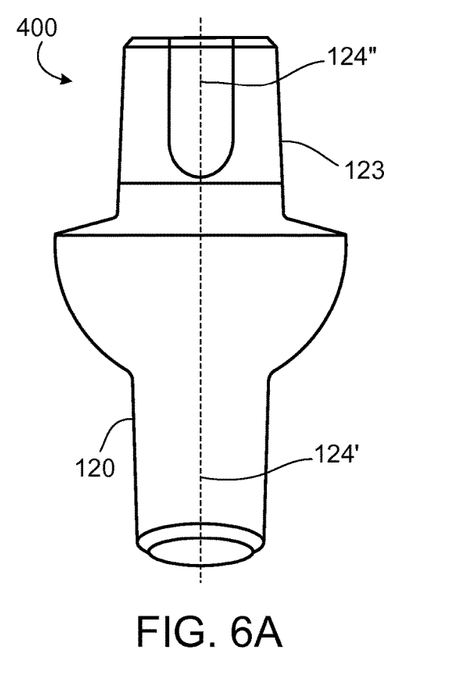
FIGS. 6A and 6B are, respectively, a front view and a side cross-sectional view of an angled dental abutment
Figure 6B:
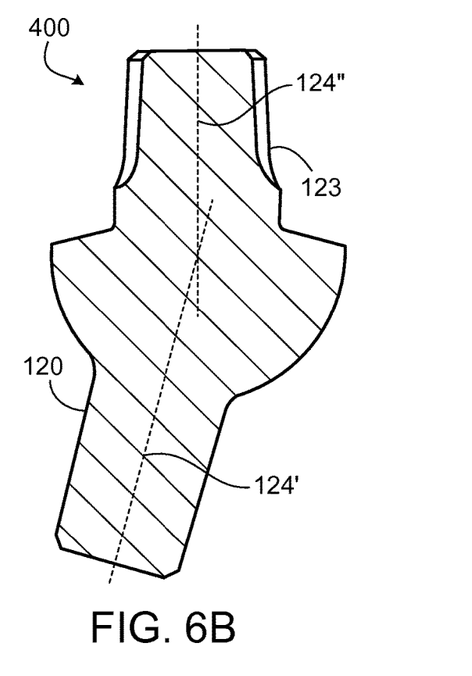

This specification has described a dental prostheses system including versatile abutments with numerous advantages. Dentists may now make numerous uses and modifications of and departures from the specific embodiments and techniques disclosed herein without departing from the inventive concepts. For example, multiple dental abutments as described above can be used to support a single dental prosthesis. FIGS. 5A-5C show a system in which four dental abutments 100 are used to support a single dental prosthesis 114. In another example, dental abutments can be formed with the features described above but with the post set at angle relative to the coronal portion. FIGS. 6A and 6B show a dental abutment 400 in which an axis 124' of the post 120 set at angle relative to an axis 124" of the coronal portion 123. Consequently, the claims are to be construed as embracing each and every novel feature and novel combination of features presented in or possessed by the apparatus and techniques herein disclosed.

There has been described novel apparatus and techniques in connection with dental implanting. It is evident that those skilled in the art may make numerous modifications of and departures from the specific apparatus and techniques herein disclosed without departing from the inventive concepts. Consequently, the invention is to be construed as embracing each and every novel concept and combination of concepts disclosed herein and limited only by the spirit and scope of the appended claims.

What is claimed is:

1. A dental abutment extending from an apical end to a coronal end along a longitudinal axis, the dental abutment comprising:

a retention element with a base oriented towards the apical end of the dental abutment and a shoulder oriented towards the coronal end of the dental abutment, the shoulder oriented at an angle of between 12.5° and 20° relative to a plane that is perpendicular to the longitudinal axis such that a perimeter of the retention element increases with increasing distance from the coronal end of the dental abutment through the shoulder;

a post extending from the apical end of the dental abutment to the base of the retention element; and a head extending from the coronal end of the dental abutment to the shoulder of the retention element, the head having a cone angle between 2.5° and 3.5°;

wherein the dental abutment has a widest point at a margin defined between the base and the shoulder of the retention element; and wherein a perimeter of the dental abutment taken in the plane perpendicular to the longitudinal axis increases without decreasing from the coronal end to the margin defined between the base and the shoulder of the retention element.

2. The dental abutment of claim 1, wherein the head defines two anti-rotational grooves on diametrically opposite sides on the coronal end.

3. The dental abutment of claim 2, wherein each groove extends from the coronal end towards the apical end and is configured to receive a securing element on a prosthesis which has a conical support face.

4. The dental abutment of claim 1, wherein the post has an apical taper angle between 1.1° and 1.6°.

5. The dental abutment of claim 1, wherein the angle of the shoulder relative to the plane that is perpendicular to the longitudinal axis is greater than 15°.

6. The dental abutment of claim 1, wherein the head comprises a bevel at the coronal end, a cylindrical portion adjacent the retention element, and an angled portion extending between the bevel and the cylindrical portion.

7. The dental abutment of claim 6, wherein the angled portion has a length from the bevel to the cylindrical portion and a cone angle such that all edges of the dental abutment can be seen when scanned from above.

8. The dental abutment of claim 1, wherein the dental abutment provides an approximation of a hemispherical contour in the base of the retention element.

9. The dental abutment of claim 1, wherein the head has a grit-blasted roughened surface to facilitate prosthetic retention.

10. The dental abutment of claim 1, wherein the head has asperities of between 100 and 300 microns in size.

11. A dental prosthesis system comprising:
a plurality of dental abutments as per claim 1, wherein the base of the retention element each dental abutment includes a hemispherical portion and cylindrical portion disposed between the hemispherical portion and the shoulder of the retention element;
wherein the plurality of dental abutments includes dental abutments with retention portions with cylindrical portions that have different lengths.

12. The dental prosthesis system of claim 11, comprising a set of transfer impression sleeves, waxing sleeves, or temporization sleeves.

13. The dental prosthesis system of claim 11, wherein the angle of the shoulder relative to the plane that is perpendicular to the longitudinal axis is between 12.5° and 20°.

14. The dental prosthesis system of claim 11, wherein the head comprises a bevel at the coronal end, a cylindrical portion adjacent the retention element, and an angled portion extending between the bevel and the cylindrical portion.

15. The dental prosthesis system of claim 14, wherein the angled portion has a length from the bevel to the cylindrical portion and a cone angle such that all edges of the dental abutment can be seen when scanned from above.

16. The dental abutment of claim 1, wherein the shoulder has a width of greater than 0.02 inches and a ratio of a distance from the coronal end to the shoulder to the shoulder width is less than seven.

17. A dental abutment extending from an apical end to a coronal end along a longitudinal axis, the dental abutment comprising:
a retention element with a base oriented towards the apical end of the dental abutment and a shoulder oriented towards the coronal end of the dental abutment, the shoulder oriented at an angle of between 12.5° and 20° relative to a plane that is perpendicular to the longitudinal axis such that a perimeter of the retention element increases with increasing distance from the coronal end of the dental abutment through the shoulder;
a post extending from the apical end of the dental abutment to the base of the retention element; and
a head extending from the coronal end of the dental abutment to the shoulder of the retention element, the head having a cone angle between 2.5° and 3.5°;
wherein the dental abutment has a widest point at a margin defined between the base and the shoulder of the retention element; and
wherein a perimeter of the dental abutment taken in the plane perpendicular to the longitudinal axis increases without decreasing from the coronal end to the margin defined between the base and the shoulder of the retention element.

* * * * *